(12) United States Patent
Tvaska et al.

(10) Patent No.: US 7,467,013 B2
(45) Date of Patent: Dec. 16, 2008

(54) RING CONNECTOR FOR IMPLANTABLE MEDICAL DEVICES

(75) Inventors: Devon N. Tvaska, Minneapolis, MN (US); Gregory L. Sundberg, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 364 days.

(21) Appl. No.: 11/190,591

(22) Filed: Jul. 27, 2005

(65) Prior Publication Data
US 2005/0261745 A1 Nov. 24, 2005

Related U.S. Application Data

(63) Continuation of application No. 10/374,037, filed on Feb. 25, 2003, now Pat. No. 7,003,351.

(51) Int. Cl.
*A61N 1/375* (2006.01)
(52) U.S. Cl. .......................................... 607/37; 439/909
(58) Field of Classification Search .................. 607/37; 439/909
See application file for complete search history.

(56) References Cited

U.S. PATENT DOCUMENTS

| | | | |
|---|---|---|---|
| 3,107,966 A * | 10/1963 | Bonhomme | 439/843 |
| 4,112,953 A * | 9/1978 | Shanker et al. | 607/37 |
| 4,934,666 A | 6/1990 | Balsells | |
| 5,730,628 A * | 3/1998 | Hawkins | 439/843 |
| 5,739,671 A | 4/1998 | Hamada | |
| 5,769,671 A | 6/1998 | Lim | |
| 6,029,089 A | 2/2000 | Hwkins et al. | |
| 6,044,302 A | 3/2000 | Persuitti et al. | |

OTHER PUBLICATIONS

"U.S. Appl. No. 10/374,037, Amendment and Response filed Jul. 27, 2005 to Non-Final Office Action mailed Jun. 29, 2005", 6 pgs.
"U.S. Appl. No. 10/374,037, Non-Final Office Action mailed Jun. 29, 2005", 4 pgs.

* cited by examiner

*Primary Examiner*—Kennedy J Schaetzle
(74) *Attorney, Agent, or Firm*—Schwegman, Lundberg & Woessner, P.A.

(57) ABSTRACT

An electrical contact for use in the header assembly of an implantable tissue stimulator includes a metal housing having a base and a sidewall where the opening in the base is adapted to receive the terminal of a medical lead therethrough. An electrical contact support member is welded to the edge of the sidewall and affixed to the support member are a plurality of spring members that are tangent to an imaginary circle whose diameter is slightly less than the outside diameter of the lead terminal contact rings. When the contacts are axially aligned in the device header, the terminal of an electrical lead may be longitudinally inserted into the header to establish electrical contact with device feedthrough wires that are joined to the electrical contacts in the header.

4 Claims, 4 Drawing Sheets

RING CONNECTOR FOR IMPLANTABLE MEDICAL DEVICES

CROSS-REFERENCE TO RELATED APPLICATION

This application is a continuation of application Ser. No. 10/374,037, filed Feb. 25, 2003, now U.S. Pat. No. 7,003,351, and entitled "Ring Connector for Implantable Medical Devices".

BACKGROUND OF THE INVENTION

I. Field of the Invention

This invention relates generally to implantable electronic tissue stimulating apparatus of the type including a pulse generator that is coupled through a medical lead to target tissue, and more particularly to the design of electrical contacts used in a header of such a pulse generator to mechanically and electrically couple the pulse generator's input/output pins to a proximal terminal of a medical lead.

II. Discussion of the Prior Art

Over the past 30 years great strides have been made in increasing the functional performance of and decreasing the physical size of implantable medical devices, such as those designed for cardiac rhythm management and neural stimulation. Generally speaking, current state-of-the-art implantable medical tissue stimulating devices incorporate a battery power supply and a microprocessor-based controller that is designed to control a pulse generator, causing it to issue pulses at times determined by the microprocessor-based controller. The pulses are conveyed to target tissue on or in the heart by means of one or more medical leads having sensing/stimulating electrodes at a distal end and the electrodes are connected by lead conductors to electrical contacts on a connector pin located at the proximal end of the lead. The lead connector connects the lead to the pulse generator.

While a variety of lead connectors have been devised, a major improvement in lead connectors has been the low profile, in-line bipolar design. An in-line connector places both electrical terminals on a single lead pin, with an insulating barrier separating the anode contact from the cathode contact. To facilitate compatibility between pulse generators and leads of differing manufacturers, standards have been developed. More particularly, a collaborative effort between IEC and International Standards Organization has defined the parameters of a low-profile connector referred to as IS-1 for unipolar and bipolar leads and DF-1 for defibrillator leads. Additionally, there is ongoing work to develop AAMI and potentially ISO standards for connectors for tripolar and quadrapolar leads.

As those skilled in the art appreciate, the lead connector must be mechanically and electrically secured to the implantable device in a way that remains secure following implantation, but which can be readily detached if and when it becomes necessary to install a new pulse generator. The Persuitti et al. U.S. Pat. No. 6,044,302 describes a connector port for an implantable pulse generator that can accommodate a plurality of in-line lead terminal pin having multiple contacts. In the '302 patent, a lead port has one or more connector blocks each including a set screw to lock the lead connector in contact with the connector block. The connector blocks are, in turn, connected to a feed-through wire. A single elastomeric seal is provided within the port such that when the connector pin is inserted therethrough, it precludes ingress of body fluids into the bore in the header. It is also known in the art to provide sealing rings on the lead terminal connector itself for creating a fluid impervious seal upon insertion of the lead's terminal into a connector port. In this regard, reference is made to the Hawkins et al. U.S. Pat. No. 6,029,089.

Copending application Ser. No. 10/222,151 filed on Aug. 16, 2002, and entitled "Connector Port Construction Technique for Implantable Medical Device", which application is assigned to the assignee of the present application, there is described a connector port for an implantable medical device that is capable of accommodating multiple feedthrough wires and lead connector contacts and that is small in size, easy to assembly and which exhibits a low insertion force. The lead connector contacts described in the aforereferenced application (referred to herein as a toroidal spring design) comprise a metal housing having a circular bore formed through the thickness dimension thereof. The wall defining the bore includes an annular recess for containing a canted-coil spring that is formed as a ring. A number of such electrical contacts are concentrically aligned in a molded plastic header with elastomeric seals disposed between each such contact. A feedthrough wire on the pulse generator is then welded to the housing containing the canted-coil spring. Upon insertion of a lead terminal, the spring is spread to receive a terminal contact therein and the coil spring engages the terminal contact at a multiplicity of points around its circumference.

The use of the currently available spring design is not optimal. The toroidal spring "floats" within the bore of the housing comprising the contact and makes connection between the terminal and spring, and in turn, between the spring and contact housing only through physical interference. This can lead to an unnecessarily high resistance connection between the connector contact member and the contacts on the lead's terminal pin. Other spring designs for this application are too large to fit within the required space or also float within their housing.

It is accordingly a principal object of the present invention to provide a small, improved, cost effective connector contact for use in the header of an implantable pulse generator and which provides a more positive connection between a feedthrough wire of the pulse generator and a lead terminal.

SUMMARY OF THE INVENTION

The present invention provides an electrical connector contact for use in the header assembly of an implantable cardiac rhythm management device for mating with a terminal pin of a tissue stimulating/sensing lead. The contact connector comprises a metal housing that has a base and a sidewall. A central opening in the base is sized to receive a terminal pin of a medical lead therethrough with a predetermined non-contact clearance. A plurality of spring members are attached to an electrical contact support member where the support member has an outside shape permitting placement on an exposed edge of the sidewall of the housing. The spring members are attached to the contact support member such that they project inwardly of the inside opening of the electrical contact support member to provide an interference fit with a lead terminal pin that is inserted through the opening in the base of the housing and through the electrical contact support member.

In one embodiment, the spring members are generally shaped to provide an interference fit with minimal drag, allowing compression thereof when the terminal pin of the tissue stimulating lead is inserted. In an alternative embodiment, the electrical contacts are bent cylindrical bars having one end welded to the contact support member and a straight section oriented tangent to a circle that is centered with respect to the opening in the base and of a lesser diameter than the opening in the base.

DESCRIPTION OF THE DRAWINGS

The foregoing features, objects and advantages of the present invention will become apparent to those skilled in the art from the following detailed description of a preferred embodiment, especially when considered in conjunction with the accompanying drawings in which.

DESCRIPTION OF THE PREFERRED EMBODIMENTS

Figure 1:
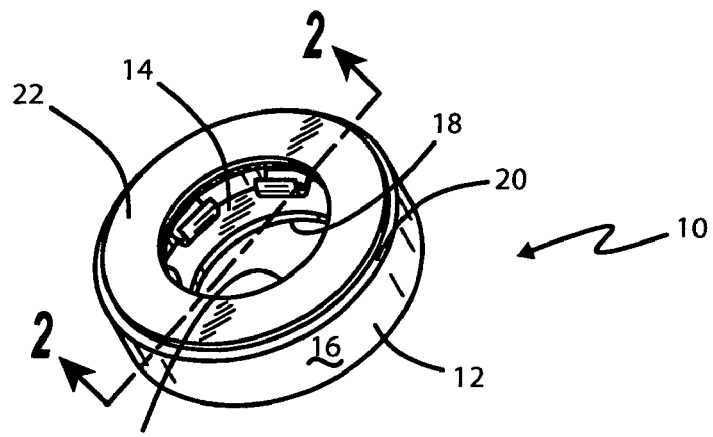
FIG. 1 is an isometric view of a ring connector comprising a first preferred embodiment.

Referring to FIG. 1, there is shown a ring connector for use in the header of an implantable tissue stimulator, such as a cardiac pacemaker or an automatic implantable cardiac defibrillator. The ring connector may be used in the manner fully described in the aforereferenced co-pending application Ser. No. 10/222,151, which is hereby incorporated by reference. It is seen to comprise a housing member 12 made of a suitable metal. It had a base 14 and a sidewall 16, where the base 14 includes an opening 18 that is of a predetermined size slightly larger than the diameter of a lead terminal that is to be inserted therethrough. As a result, there is a predetermined non-contact clearance between the opening and the lead terminal. Resting atop the exposed edge 20 of the metal contact housing 12 is a washer-like plate 22 that is welded to the exposed edge 20 of the housing. The central opening 24 of the washer 22 is generally sized such that a lead terminal will also have a non-contact clearance with the washer 22.

Figure 2:
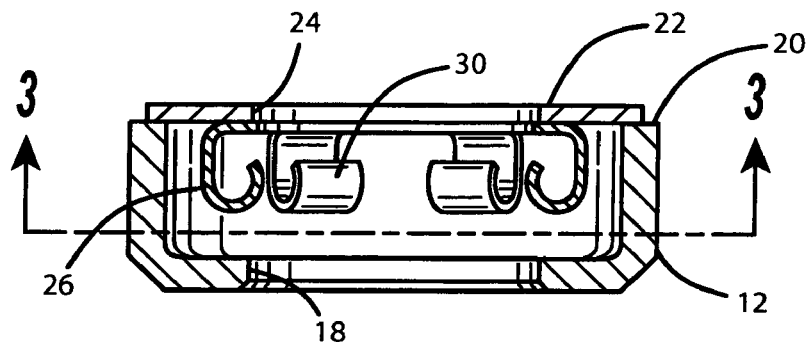
FIG. 2 is a cross-sectional view taken along the line 2-2 in FIG. 1.
Figure 4:
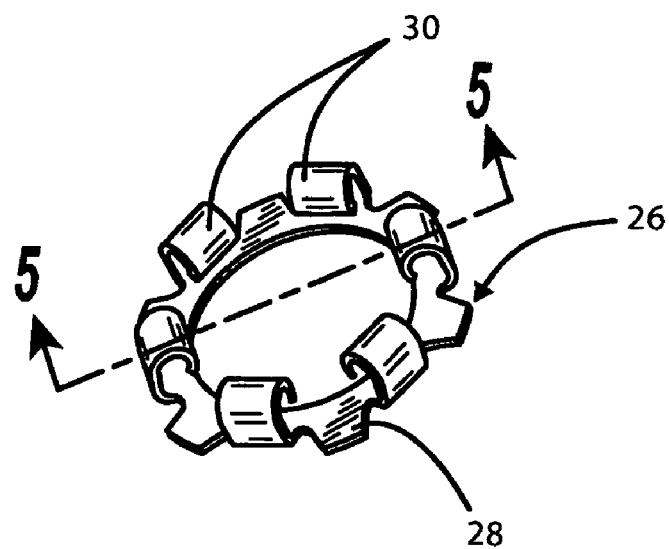
FIG. 4 is an isometric view of a contact ring used in the assembly of the embodiment of FIG. 1.

As seen in the cross-sectional view of FIG. 2, a spring contact member 26 is welded to the washer 22. Referring momentarily to FIG. 4, the spring contact member 26 is made of a suitable metal, such as MP35N. In a preferred form, the contact members are formed with the ring 28 in a stamping and bending operation.

Figure 5:
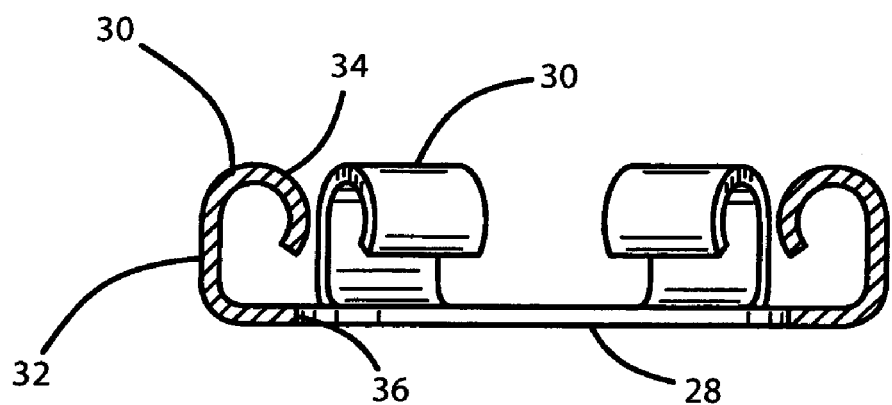
FIG. 5 is a cross-sectional view along the line 5-5 in FIG. 4.

The cross-sectional view of FIG. 5 shows that the contacts 30 of the member 26 are generally shaped to provide interference with minimal drag, having a straight back portion 32 that is generally perpendicular of the plane of the ring 28 and an arcuate front portion 34. The curvature of the front portion 34 is such that it is tangent to an imaginary circle that is of a lesser diameter than the opening in member 28 and the openings 18 and 24 seen in FIG. 1.

Figure 3:
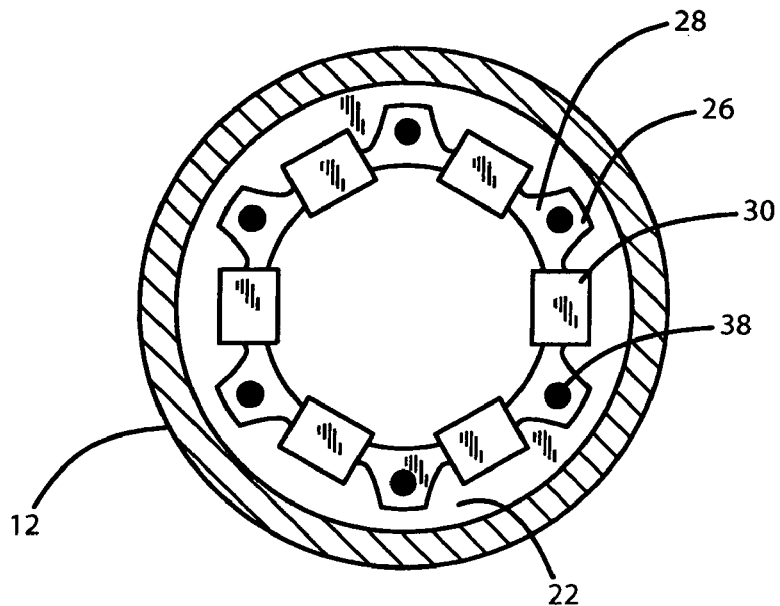
FIG. 3 is a cross-sectional view taken along the line 3-3 in FIG. 2.

Referring next to the cross-sectional view of FIG. 3, it can be seen that the contact member 26 of FIG. 4 is welded at points represented by the black dots 38 in the drawing to the washer 22 and that the contacts 30 encroach into the opening defined by the aperture of the contact support member 26. The tolerances are such that when a lead terminal is inserted through the opening 18 in the housing member 12 with a predetermined force, it will deflect the springs 30 which then intimately engage a contact ring on the lead terminal to establish electrical contact at a multiplicity of points, resulting in a low impedance connection.

While the embodiment described illustrates six contacts 30 on the spring contact member 26, a greater or a fewer number of such contacts may be utilized. As a minimum, however, there should be at least three such contacts, but with six such contacts being preferred. The contacts 30 will be deflected as the lead terminal is inserted through the ring connector 10. While the embodiment reflected in FIGS. 1-5 show the contact ring 28 spot-welded to the underside of washer 22, it is also possible to insert the contact ring 28 into the housing with the contacts 30 projecting upward from the base 14.

Figure 8:
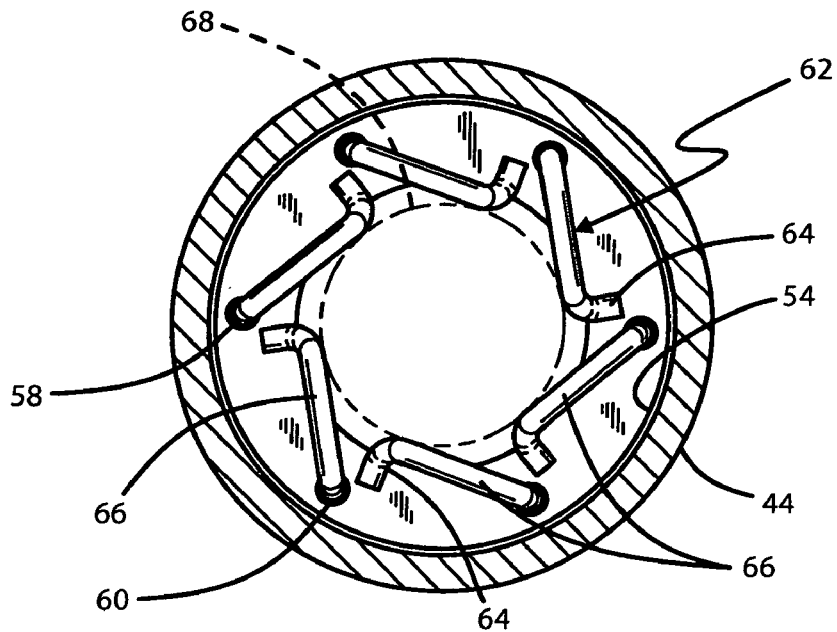
FIG. 8 is a cross-sectional view taken along the line 8-8 in FIG. 7.
Figure 9:
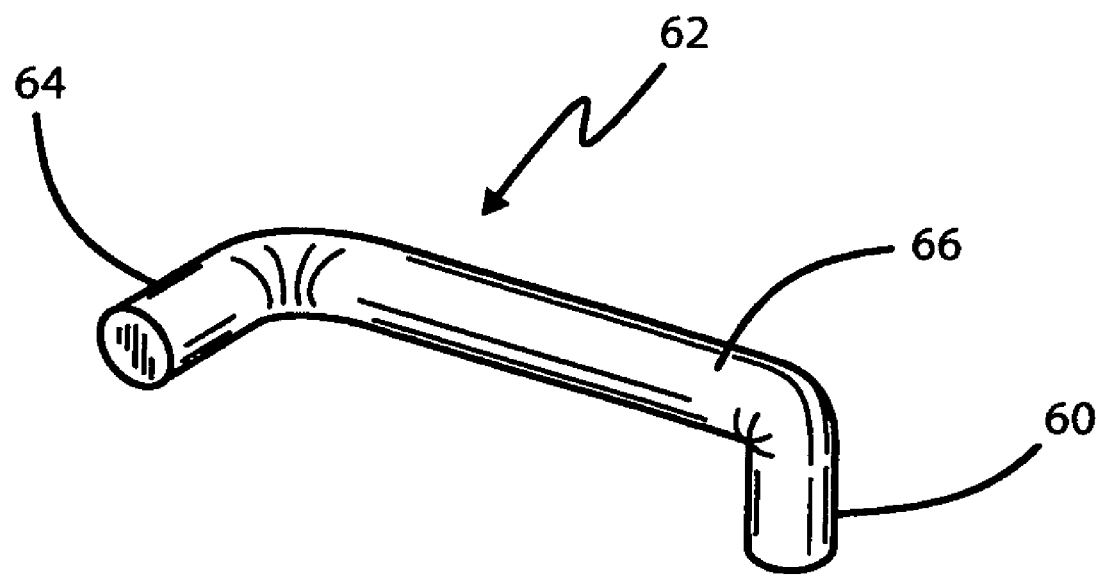
FIG. 9 is an isometric view of one of the contacts used in the embodiment of FIG. 6.

FIGS. 6-9 illustrate an alternative embodiment of the ring connector of the present invention. The ring connector, indicated generally by numeral 40, again comprises a metal contact housing 42 having a sidewall 44 supported on a base 46. The base has an opening 48 formed therethrough that is sized to receive a lead terminal with non-contact clearance. Again, the size of the opening 48 is slightly greater than the diameter of a ring contact on a medical lead to be inserted through that aperture. The aperture 48 is preferably beveled, as at 50, to facilitate or guide the insertion of a lead's terminal therethrough. Welded to an exposed edge 52 of the wall 44 is a contact plate 54 in the form of a washer having an opening 56 that is seized to receive a lead terminal with non-contact clearance. At regular intervals, e.g., every 60°, a small hole, as at 58, is drilled through the contact support member 54. Fitted into each of these holes is one end 60 of a generally bent cylinder contact 62. An isometric view of one such bent cylinder contact is shown in FIG. 9.

Referring to FIG. 8, before being welded in place within the holes 58, the contacts 62 are aligned in a manufacturing jig (not shown) so that the straight section 66 of the bent cylinder is tangent to an imaginary circle represented by the broken line 68 in FIG. 8 and bent end portion 64 is directed away from that circle. When a lead terminal is inserted through the contact member assembly 40, the cylindrical bar contact 62 will be deflected so as to press against a contact surface of the lead's terminal to establish a low resistance path between the pulse generator (not shown) that attaches to the housing 42 and the aforesaid lead contact surface.

Figure 6:
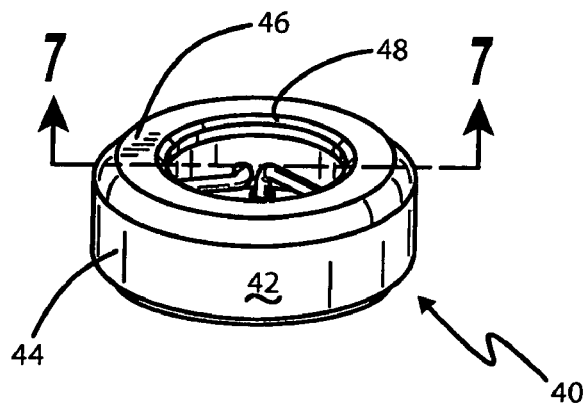
FIG. 6 is an isometric view of an alternative preferred embodiment of the invention.
Figure 7:
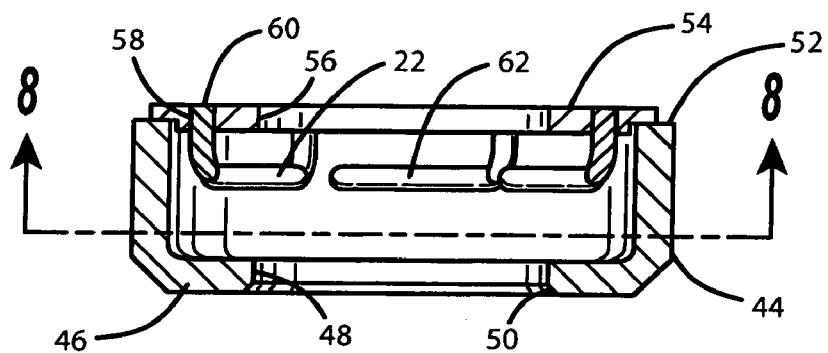
FIG. 7 is a cross-sectional view taken along the line 7-7 in FIG. 6.

When the ring contact assemblies 10 and 40 of FIG. 1 or FIG. 6, respectively, are axially aligned in the header of an implantable medical device of the type concerned here, they electrically couple the device's high or low voltage output to a corresponding medical lead terminal. No outside mechanical actuation or tools are required, such as set screws or Allen wenches. In addition, the contact assemblies of the present invention are less costly than known prior art ring contact arrangements.

The physical geometry of the contacts disclosed herein is quite different from known prior art approaches. The spring tabs or bent cylinders of the present invention, instead of the canted toroidal springs of the prior art, yield improved results. The prior art competitive contact has an inherent disadvantage in that its toroidal spring "floats" within the housing and makes connection between the terminal and housing only through physical interference. The contacts disclosed in the present application are solidly connected (i.e., welded) to the housing, thus improving the electrical quality of the connection.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An electrical contact for use in the header assembly of an implantable cardiac rhythm management device for mating with a terminal pin of a tissue stimulating lead, the electrical contact comprising:
   a metal retainer having a base with a sidewall, the base having an opening formed therethrough sized to receive a lead terminal pin therethrough with a predetermined non-contact clearance;
   a flat, conductive toroidal electrical contact support member having an outside shape permitting placement of said support member on an exposed edge of the sidewall of the metal retainer and a central opening of a diameter generally equal to that of the opening formed in the base of the metal retainer; and
   a plurality of spring contact members, each comprising a metal wire having a straight central portion, a first end portion bent to the axis of the straight central portion and a second end portion bent to the axes of both the straight portion and the first end portion, the plurality of spring coact members having their second end portions attached to one of the electrical contact support member and the base such that the straight portions are oriented tangent to an imaginary circle that is centered with respect to the opening in the base, said imaginary circle being of a lesser diameter than said opening in the base.

2. The electrical contact as in claim 1 wherein the plurality of spring contact members is attached by welding to the electrical contact support member.

3. The electrical contact as in claim 1 wherein the contact support member supports at least three of said spring contact members.

4. The electrical contact as in claim 1 wherein the contact support member supports six of said spring contact members.

* * * * *